United States Patent [19]

Uher

[11] Patent Number: 5,477,156
[45] Date of Patent: Dec. 19, 1995

[54] DETONATION WAVE DETECTION PROBE INCLUDING PARALLEL ELECTRODES ON A FLEXIBLE BACKING STRIP

[75] Inventor: Kenneth J. Uher, Los Alamos, N.M.

[73] Assignee: The Regents of the University of California, Alameda, Calif.

[21] Appl. No.: 454,894

[22] Filed: May 31, 1995

Related U.S. Application Data

[63] Continuation of Ser. No. 141,297, Oct. 21, 1993, abandoned.

[51] Int. Cl.$^6$ .................................................. G01N 33/22
[52] U.S. Cl. ............................................ 324/715; 324/724
[58] Field of Search ................. 73/35; 310/311, 310/338, 351, 365, 370; 324/71.1, 72.5, 713, 715, 724, 754

[56] References Cited

U.S. PATENT DOCUMENTS

| | | | |
|---|---|---|---|
| 3,528,280 | 9/1970 | Ciccone et al. | 73/35 |
| 3,852,994 | 12/1974 | Pereda | 73/35 |
| 3,978,731 | 9/1976 | Reeder et al. | 73/407 PR |
| 4,533,415 | 8/1985 | Wagner, III et al. | 149/35 |
| 4,649,339 | 3/1987 | Grangroth et al. | 324/158 P X |
| 4,734,044 | 3/1988 | Radice | 310/365 |
| 4,975,638 | 12/1990 | Evans et al. | 324/158 P X |
| 5,159,301 | 10/1992 | Kaida et al. | 310/370 |

OTHER PUBLICATIONS

AMP Incorporated, "Piezo Film Sensors" Brochure, Oct. 1993, p. 4.

Primary Examiner—Kenneth A. Wieder
Assistant Examiner—Christopher M. Tobin
Attorney, Agent, or Firm—Richard J. Cordovano

[57] ABSTRACT

A device for sensing the occurrence of destructive events and events involving mechanical shock in a non-intrusive manner. A pair of electrodes is disposed in a parallel configuration on a backing strip of flexible film. Electrical circuitry is used to sense the time at which an event causes electrical continuity between the electrodes or, with a sensor configuration where the electrodes are shorted together, to sense the time at which electrical continuity is lost.

6 Claims, 1 Drawing Sheet

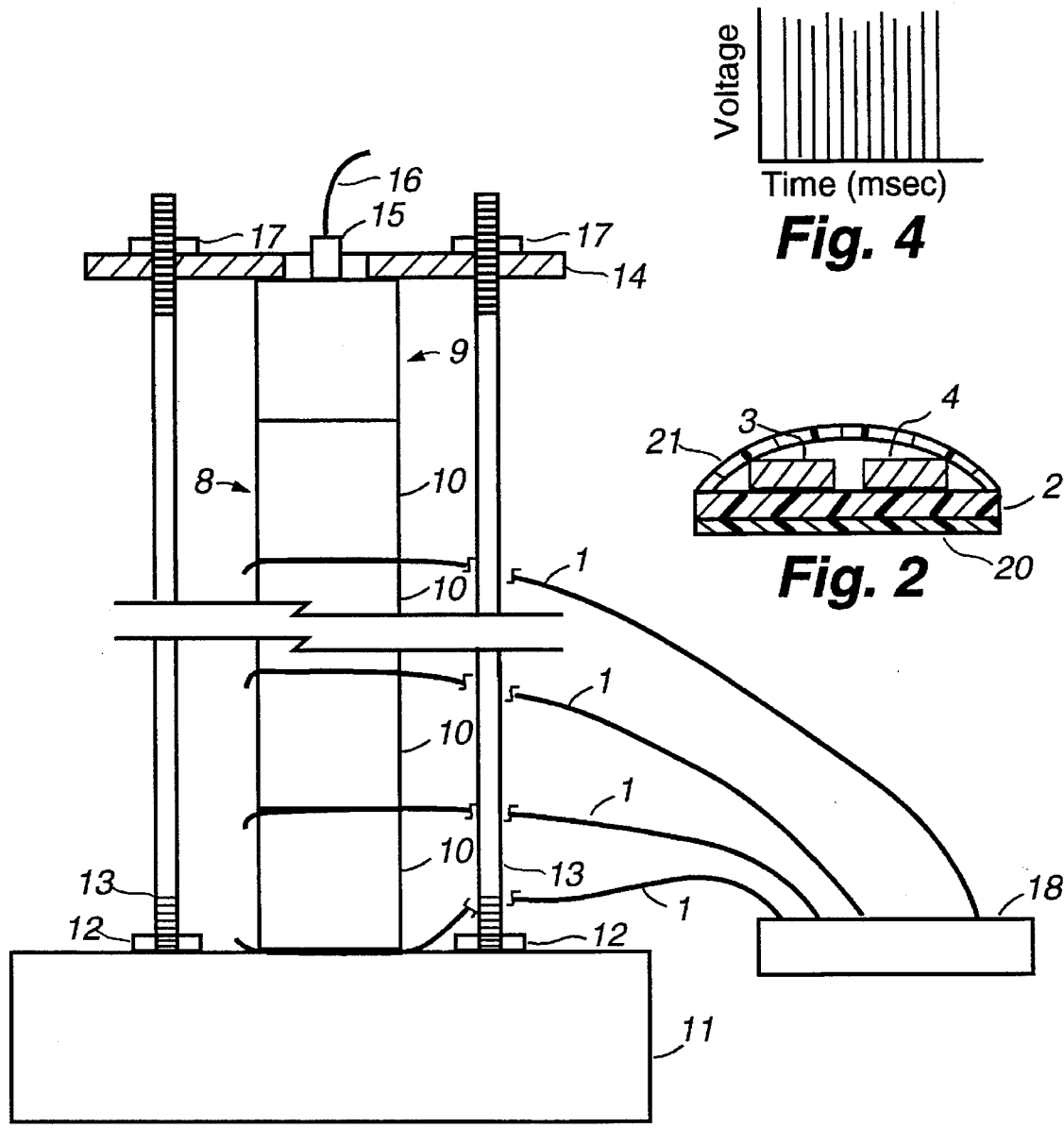
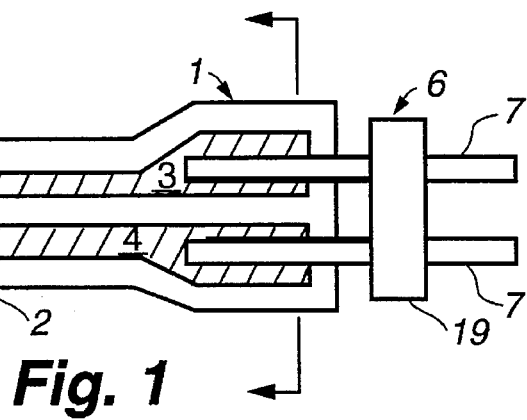

DETONATION WAVE DETECTION PROBE INCLUDING PARALLEL ELECTRODES ON A FLEXIBLE BACKING STRIP

This invention was made with government support under Contract No. W-7405-ENG-36 awarded by the U.S. Department of Energy. The government has certain rights in the invention. This is a continuation of application Ser. No. 08/141,297 filed on Oct. 21, 1993, now abandoned.

BACKGROUND OF THE INVENTION

The present invention was born of a need for a better method of measuring detonation velocity. An explosive chemical reaction is initiated at one point in a mass of explosive material by means such as an electrical potential or ignition of a different explosive used as a detonator. All of the explosive material does not react at the same time; starting at the initiation point, a reaction front moves through the mass of material at a very rapid rate, so rapidly that it appears as if the entire mass of explosive reacted at once. The moving reaction front, or zone in which the reaction is taking place, is commonly called a detonation wave. In testing of explosives, it is necessary to determine the detonation velocity of an explosive, which is the speed at which the detonation wave travels though a mass of the explosive. A detonation wave is electrically conductive. A method of measuring detonation velocity is to place pairs of fine wires at locations within a mass of explosive and note the times at which there is electrical continuity between each pair of wires. The time of arrival of the detonation wave is the time at which electricity will flow from one wire of a pair to another.

Placing pairs of fine copper wires at locations in an explosive in setting up a test is difficult and time consuming. The wires must be of small diameter in order that they do not affect the characteristics which the test is designed to measure. Wires used in testing and experimentation such as the exemplary test described herein have a diameter of 0.002 inch. They tend to tangle and break and shift position. Loss of data points due to problems with detonation wave sensing wires may necessitate repeating an experiment. The present invention solves these problems and provides a sensor with many uses in addition to that which impelled its development.

BRIEF SUMMARY OF THE INVENTION

This invention is a device for sensing the occurrence of destructive events and events involving mechanical shock in a non-intrusive manner. A pair of electrodes is disposed in a parallel configuration on a backing strip of flexible film. Electrical circuitry is used to sense the time at which an event causes electrical continuity between the electrodes or, with a sensor configuration where the electrodes are shorted together, to sense the time at which electrical continuity is lost.

It is an object of the invention to provide a sensor which is sufficiently inexpensive that it can be used in tests which destroy it.

It is another object of the invention to provide a sensor which facilitates more rapid set-up of test detonations of explosives.

It is another object of the invention to provide a sensor which is sufficiently rugged so that it is easily handled without danger of damage.

It is a further object of the invention to provide a sensor which is of small size, so that it does not change the characteristics of the event in which it is used.

In one embodiment, this invention is a backing strip of a thin flexible polymeric film; two elongated electrodes of an electrically conductive material, where each electrode has the form of a thin flexible film having a first major surface, a second major surface, a first end, and a second end, where said electrodes are disposed on said backing strip parallel to one another and separated from one another by a gap of substantially constant width, and where said first major surface of each electrode is attached to said backing strip; and connector means attached to said first end of each electrode.

SUMMARY OF THE DRAWINGS

FIG. 1 is a top view of an event sensor.

FIG. 2 is a section view of the event sensor of FIG. 1 taken as shown by the section arrows of FIG. 1.

FIG. 3 depicts a test assembly with a stack of pellets of an explosive and event sensors located between the pellets.

FIG. 4 is a depiction of a oscilloscope trace of data obtained upon detonation of the explosive of the test assembly shown in FIG. 3.

DETAILED DESCRIPTION OF THE INVENTION

Referring now to FIGS. 1 and 2, event sensor 1 is described. Backing strip 2, which is a thin flexible polymeric film, has electrode 3 and electrode 4 attached to it. Each electrode is electrically conductive and has the form of a thin flexible film. Break lines are shown in FIG. 1, as an event sensor is normally longer than the sensor of FIG. 1. Connector means 6 is attached to one end of electrodes 3 and 4 at one end of the backing strip. The width of the electrodes is greater at this end in order to facilitate soldering connector means 6 to the electrodes or to accommodate other methods of attaching connector methods to the electrodes. The connector means may be any convenient means for independently connecting each electrode to electrical circuit means or, as shown in FIG. 1, may be a standard printed circuit board (PCB) connector having a non-conductive plastic body 19 and two pins denoted by reference number 7. Pins 7 provide an electrical current path from each electrode to a standard electronic breadboard to which electrical circuit means are connected to provide electrical power and to carry information to means for storing and displaying data.

It is convenient to manufacture the sensors in a normally closed configuration, that is, with the electrodes electrically connected to one another by means of a thin flexible film of an electrically conductive material attached to backing strip 2 in the same manner as electrodes 3 and 4. Reference number 5 denotes the connector in FIG. 1. When it is desired to use a sensor in a normally open configuration, the end of the sensor is snipped off with scissors such that connector 5 is removed and the electrodes are electrically isolated from one another.

A exemplary use of the invention is described by reference to FIG. 3. A conventional explosive material which is part of a nuclear weapon is removed from the weapon for testing to verify that the explosive retained certain characteristics during storage of the weapon. Cylindrical pellets of the explosive having a diameter of one inch and a height of one inch are machined from the removed explosive. Twelve pellets 10 are stacked one on top of another to form rate stick 8. As can be seen from the break lines in FIG. 3, not all pellets are shown in the drawing. Detonator assembly 9 has the same dimensions as each pellet and is located at the top of the stack of pellets, i.e., rate stick 8. Detonator assembly 9 is a plastic fixture holding detonator 15 and a quantity of detonating explosive. An electrical current is provided to detonator 15 by means of detonator wire 16 in order to detonate the explosive contained in assembly 9, thus causing detonation in the topmost pellet of the stack. A detonation wave then moves downward through the stack of pellets.

The rate stick rests on a 2 inch thick cold rolled steel base 11, which has threaded rods 13 attached to it by means of nuts 12, which are glued to the steel base. Hold down disk 14 is circular with a circular opening at the center to accommodate detonator 15. Hold down disk 14 is shown in section with hatching in order to facilitate an understanding of the drawing. Nuts 17 thread onto rods 13 and are tightened to cause hold down disk 14 to bear against detonator assembly 9 and to hold the detonator assembly and the stack of pellets in position. Only two of the three threaded rods which are used are shown.

Event sensors 1 are shown in "edge view" and are located between the pellets of explosive and below the bottom pellet of the rate stick. Each sensor has an overall length of about 16 inches and the width of the backing strip is about 3 mm. Each electrode has a width of about 0.5 mm over most of its length and the width at the portion to which the electrode is attached is about 2 mm. The length of the wide portion of each electrode is about 10 mm. The event sensors plug into breadboard 18 by means of pins 7 (FIG. 1). There are a total of twelve event sensors connected to breadboard 18, though only four event sensors are shown in FIG. 3. Breadboard 18 is shown detached from base 11, but is actually attached to it, so that the test assembly can be put together in a shop and transported to the site where the rate stick is exploded. The sensors are used in a normally open mode. After the test assembly is set in place at the detonation site and wiring leading to an oscilloscope (not shown) is connected to the breadboard, electrical continuity through each sensor is checked. Then the end of each sensor is cut off to convert the normally closed sensors, as shown in FIG. 1, to a normally open configuration.

As the detonation wave travels downward in the rate stick, it provides a conductive path between the electrodes of each sensor, in turn. One electrode of each sensor is energized. Before each sensor is destroyed by the explosion, the circuit of a sensor is completed by the detonation wave so that current flows from the energized electrode of the sensor to the non-energized electrode. This current flow is sensed and recorded. The signals generated are displayed on an oscilloscope, as depicted in FIG. 4. Each vertical line on FIG. 4 represents the voltage recorded when the detonation wave arrived at the location of an event sensor and completed the circuit in the sensor. Velocity at which the detonation wave traveled through each pellet is determined from the time between circuit completions in the sensors immediately above and below each pellet. In this test, the velocity of the detonation wave through each pellet was about the same, as can be seen by the even spacing of the voltage spikes. The explosion causes a depression to form in the surface of the base located under the rate stick. The depth of the depression is an indicator of the force generated during detonation of the rate stick.

One method of manufacturing the event sensors is as follows. A 0.0005 inch thick layer of copper is deposited on a 0.0005 inch thick sheet of Kapton (trademark of E. I. DuPont de Nemours and Company) polyimide film. Areas of copper are removed from the Kapton film by a process comprising applying a photopolymer film over the copper, placing a mask over the photopolymer film, exposing the assembly of copper-coated film and photopolymeric film which is not covered by the mask to light from an appropriate light source, removing the mask, and subjecting the assembly to a chemical etch bath in order to remove those portions of the photopolymer film which were exposed to the light source and to remove the copper below the removed photopolymer film. After the etching step, the remaining photopolymer film is removed and the sheet of Kapton is then cut into strips, where each strip is a backing strip having copper electrodes disposed on it as shown in FIG. 1.

In order to enhance strength and durability of an event sensor, a portion of the backing strip surface opposite to the surface where the connector means is attached to the electrodes may be reinforced by laminating a reinforcing strip of a thin flexible polymeric film to the backing strip. This is shown by reinforcing strip 20 of FIG. 2. A convenient way to accomplish this during the manufacturing process described above is to apply a strip of film coated with an adhesive to the sheet of copper-coated film on the side which is not coated, prior to cutting the film into individual event sensors. Mylar® or Kapton® tape may be used and applied in a single strip perpendicular to the event sensors at the appropriate location.

In the example above, the explosive material is not conductive, so that contact between the electrodes and the material does not short out or otherwise affect the sensors. When it is necessary to isolate the electrodes from the environment in which an event sensor is used, a cover strip of a thin flexible polymeric material may be used. The cover strip is placed over the top surface of a sensor, so that it covers the electrodes, and the cover strip is attached to the backing strip. This is shown by cover strip 21 of FIG. 2. Attachment may be at several points around the perimeter or the cover strip may adhere to substantially all portions of the backing strip which are not covered by the electrodes.

There are numerous uses for the event sensor. For example, event sensors may be placed at locations within the mass of fuel in a solid-fuel rocket motor in order to sense when fuel at a particular location is consumed. They may be used to determine the exact location at which a projectile strikes reactive armor, which "explodes" when a projectile hits it. A grid of sensors having a normally closed configuration is placed in front of the armor. All of the sensors will be destroyed when the armor explodes, but before this occurs, electrical continuity is lost in the sensors directly in front of the projectile as the projectile passes through them. The time and location at which loss of continuity occurs is recorded. A sensor may be firmly attached to two points in an underwater environment so that a shock wave caused by an event is sensed by means of loss of electrical continuity in the sensor.

What is claimed is:

1. Apparatus for sensing a detonation wave by means of completion of an electrical circuit, said apparatus comprising:
   a. a backing strip of a thin flexible inert non-conductive polymeric film;
   b. two elongated electrodes of an electrically conductive material, where each electrode has the form of a thin flexible film having a first major surface, a second major surface, a first end, and a second end, where said electrodes are disposed on said backing strip parallel to one another and separated from one another by a gap of substantially constant width such that a conductive path between said electrodes may be established by a detonation wave, and where said first major surface of each electrode is attached to said backing strip; and c. connector means attached to said first end of each electrode.

2. The apparatus of claim 1 where a cover strip of a thin flexible polymeric film is disposed over said backing strip and said second major surface of each electrode, where said cover strip and the backing strip are attached to one another at least at points along the perimeter of each strip, in order to isolate the elecrodes from the environment external to the backing strip and the cover strip.

3. The apparatus of claim 1 where a reinforcing strip of a thin flexible polymeric film is laminated to a portion of the surface of said backing strip which is located opposite to the surface of the backing strip to which said first ends of said electrodes are attached.

4. Apparatus for sensing the occurrence of a destructive event by means of interruption of an electrical circuit, said apparatus comprising:

a. a backing strip of a thin flexible inert non-conductive polymeric film;

b. two elongated electrodes of an electrically conductive material, where each electrode has the form of a thin flexible film having a first major surface, a second major surface, a first end, and a second end, where said electrodes are disposed on said backing strip parallel to one another and separated from one another by a gap of substantially constant width, where said first major surface of each electrode is attached to said backing strip, where said second ends of said electrodes are electrically connected to one another by a connector of electrically conductive material in the form of a thin flexible film having a surface attached to said backing strip, and where said apparatus may be disposed such that a destructive event interrupts electrical continuity in the circuit comprised of said electrodes and said connector; and c. connector means attached to said first end of each electrode.

5. The apparatus of claim 4 where a cover strip of a thin flexible polymeric film is disposed over said backing strip and said second major surface of each electrode, where said cover strip and the backing strip are attached to one another at least at points along the perimeter of each strip, in order to isolate the elecrodes from the environment external to the backing strip and the cover strip.

6. The apparatus of claim 4 where a reinforcing strip of a thin flexible polymeric film is laminated to a portion of the surface of said backing strip which is located opposite to the surface of the backing strip to which said first ends of said electrodes are attached.

* * * * *